United States Patent [19]

Noguchi et al.

[11] Patent Number: 4,587,958
[45] Date of Patent: May 13, 1986

[54] ULTRASONIC SURGICAL DEVICE

[75] Inventors: Yasuo Noguchi, Yokohama; Masaru Shibata, Kanagawa, both of Japan

[73] Assignee: Sumitomo Bakelite Company Limited, Tokyo, Japan

[21] Appl. No.: 618,398

[22] PCT Filed: Apr. 4, 1983

[86] PCT No.: PCT/JP83/00106
§ 371 Date: Jun. 5, 1984
§ 102(e) Date: Jun. 5, 1984

[87] PCT Pub. No.: WO84/03828
PCT Pub. Date: Oct. 11, 1984

[51] Int. Cl.[4] .............................................. A61H 1/00
[52] U.S. Cl. ................................. 128/24 A; 310/316
[58] Field of Search ............ 128/24 A, 328; 310/316; 331/109; 361/203

[56] References Cited

U.S. PATENT DOCUMENTS

| | | | |
|---|---|---|---|
| 3,727,112 | 4/1973 | Popescu | 361/203 |
| 4,169,984 | 10/1979 | Parisi | 128/24 A |
| 4,223,676 | 9/1980 | Wuchinich et al. | 128/24 A |
| 4,236,510 | 12/1980 | Hatter et al. | 128/24 A |
| 4,330,278 | 5/1982 | Martin | 128/24 A X |

*Primary Examiner*—Kyle L. Howell
*Assistant Examiner*—Francis J. Jaworski
*Attorney, Agent, or Firm*—Sheridan Neimark; Karl W. Flocks; A. Fred Starobin

[57] ABSTRACT

An ultrasonic oscillation device adapted for use in surgical operations includes, for the purpose of producing ultrasonic vibrations of an amplitude and power capable of exhibiting a satisfactory tissue shattering capacity in a wide field of living tissues, an ultrasonic oscillation section having a power amplifier circuit for adjusting the amplitude of its output without any difference in phase between the output and a feedback signal, and a starting impulse reducing circuit for reducing the impulse due to a transient current upon the starting of oscillation. Also, an ultrasonic transducer includes an electrostriction type transducer and a horn, and the horn forming a scalpel portion is provided with a suction opening adapted for irrigating an affected part operated on and its surrounding, floating shattered cellular pieces and sucking and removing the floating cellular pieces.

9 Claims, 13 Drawing Figures

ULTRASONIC SURGICAL DEVICE

TECHNICAL FIELD

The present invention relates to an ultrasonic oscillation device, and more particularly to an ultrasonic oscillation device adapted for use in surgical operations.

BACKGROUND ART

While, a scalpel, is used for the purpose of incising a tissue of a living body, an electric scalpel or laser scalpel is a surgical instrument which has the function of simultaneously cauterizing tissues and cauterizing blood vessels such as capillary vessels and thereby simultaneously effecting the incision and hemostasis and which is suitable for use in the field of operations in which both the incision and hemostasis are effected. However, since these surgical instruments simultaneously effect the incision of a tissue and the cutting of blood vessels or nerves, in the case of an operation on such an affected part as a liver or brain tissue where a large number of blood vessels or nerves gather or in the case of an operation on any other affected part to be operated on where it is desirable to leave the blood vessels or nerves as such, it is rather difficult to use an electric scalpel or laser scalpel and thus a recourse is had to a scalpel made of steel or the like which has heretofore been in use.

As regards the conventional surgical instruments utilizing the tissue cutting or shattering capacity of ultrasonic vibrations, the ultrasonic surgical instruments which have been put in practical applications include those which chip bones or joints in the fields of plastic surgery and general surgery, surgical instruments for operating on cataract in the field of ophthalmology and dental instruments for removing the tartar on teeth. However, these surgical instruments utilizing ultrasonic vibrations are not designed to display ultrasonic vibrations of an amplitude and power only sufficient to extensively shatter tissues and they are each used as an exclusive surgical instrument for an extremely limited surgical field.

On the other hand, Japanese Patent Laid-Open Publication No 54-152383 (1979) discloses an ultrasonic surgical instrument having a magnetostriction type transducer composed of a laminate of nickel alloys having different mechanical characteristics and intended for application to a wide range of body tissues.

However, in the case of a magnetostriction type transducer using ferrite, for example, the transducer is strong to axial compression but weak to axial elongation and therefore the amplitude cannot be increased. Also, in the case of a nickel type magnetostriction transducer the transducer lacks in shock resistance so that the transducer tends to be damaged if a large load is applied to the forward end of the horn and also the mechanical Q inevitably becomes low as compared with the electrostriction type transducer, thus increasing the electric loss, correspondingly increasing the heat generation of the transducer and giving rise to the possibility of damaging the transducer unless the thus generated heat is removed by cooling means such as water.

Also, a known ultrasonic oscillation device employing an electrostriction type transducer is disadvantageous in that any attempt to increase the amplitude of the horn forward end causes a difference between the phase of an output power waveform for the vibration of the ultrasonic transducer and the phase of a feedback voltage waveform, thus making it impossible to increase the amplitude.

DISCLOSURE OF INVENTION

It is an object of the present invention to provide an ultrasonic oscillation device capable of producing ultrasonic vibrations of such amplitude and power sufficient to exhibit a satisfactory tissue shattering capacity in the field of wide range of living tissues.

An electrostriction type ultrasonic oscillation device according to the invention has a circuit construction such that an ultrasonic oscillation section for exciting a ultrasonic transducer includes a starting impulse reducing circuit which serves as a circuit for preventing the generation of a transient impulse current during the starting period and also a power amplifier circuit has a circuit construction adapted to make its output voltage waveform and feedback voltage waveform equal in phase. Thus, the device is advantageous in that the device is not susceptible to any load applied to the forward end of a horn and the mechanical Q can be increased thereby reducing the electric loss, decreasing the heat generation of a ultrasonic transducer and exhibiting a satisfactory durability without using any cooling means, and the device is best suited for such applications as an ultrasonic scalpel which is particularly required to have reliabily thus making it possible to cut and remove by shattering any tissue to be cut off in any affected part to be operated on, i.e., an affected part to be operated on where blood vessels or nerves gather, without hurting the blood vessels or nerves.

BRIEF DESCRIPTION OF DRAWINGS

The present invention will be apparent from the following detailed description taken in conjunction with the accompanying drawings, in which.

BEST MODE FOR CARRYING OUT THE INVENTION

Figure 1:
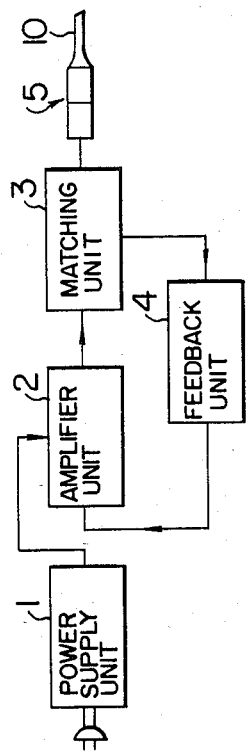
FIG. 1 is a basic block diagram of an ultrasonic oscillation device according to the invention.

Now describing an embodiment in which an ultrasonic oscillation device of this invention is applied to an ultrasonic scalpel, an ultrasonic oscillation section basically includes a power supply unit 1, an amplifier unit 2, a matching unit 3, a feed back unit 4 and an ultrasonic transducer 5 for converting electric vibratory energy to mechanical vibratory energy which are shown in FIG. 1.

Figure 2:
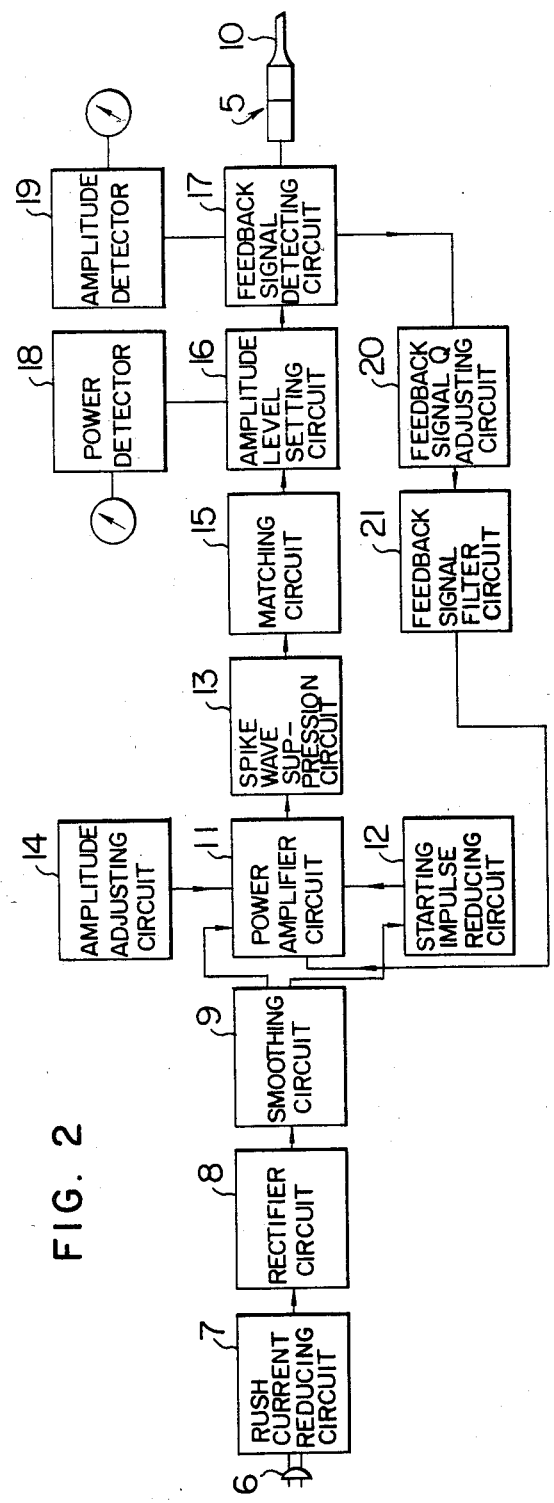
FIG. 2 is a detailed block diagram of the basic block diagram shown in FIG. 1.

Describing the details of these basic circuits in greater detail with reference to FIG. 2, in accordance with the invention the amplifier unit 2 improves on the conventional circuit construction as will be described later. The power supply unit 1 includes a rush current reducing circuit 7, a rectifier circuit 8 and a smoothing circuit 9. The power is supplied in the form of A.C. 100 V from a commercial A.C. power source 6 or a suitable voltage and it is coupled to the rush current reducing circuit 7. Since, when the power source is connected to the oscillator circuit of this ultrasonic scalpel, there is the possibility of an excessive current flowing upon the connection damaging the rectifier element in the rectifier circuit 8 which is an A.C.-D.C. converter circuit for converting an A.C. power supply to a D.C. power supply, the rush current reducing circuit 7 is provided for the purpose of reducing the possibility and the protection and stabilization of the power supply circuit are intended by means of the rush current reducing circuit 7. Also, if the ripple factor of the ripple in the D.C. waveform produced by the rectifier circuit 8 large, a mechanical vibration system formed by the ultrasonic transducer 5 and a horn 10 is made unstable and therefore the smoothing circuit 9 is provided for the purpose of reducing the ripple factor. By virtue of this smoothing circuit 9, extremely stable ultrasonic vibrations are produced at the forward end of the horn 10 or the scalpel forward end.

The amplifier unit 2 includes a power amplifier circuit 11, a starting impulse reducing circuit 12, a spike wave suppression circuit 13 and an amplitude adjusting circuit 14. Of these circuts, the power amplifier circuit 11 and the starting impulse reducing circuit 12 differ from the conventional circuits.

The power amplifier circuit 11 is of the low loss circuit type which allows continuous oscillations without any cooling. Thus, while it has been the practice to connect a resistor 54 to the base of an amplifying transistor 55 as shown in the prior art of FIG. 3, in the power amplifier circuit 11 of the invention, as shown in FIG. 4, a parallel circuit of a diode 56 and a capacitor 57 is connected to the base of an amplifying transistor 55 so that the diode 56 and the capacitor 57 facilitate the flow of a bias current even if a feedback voltage is low, and also a capacitor 59 is added in parallel with a resistor 58 between the amplifying transistor 55 and the following transistor 64 thus connecting the capacitor 59 of a predetermined capacity so as to greatly change the output voltage between the collector and emitter of the transistor 64 and thereby to prevent any deviation of the phase of a feedback signal from the feedback unit 4 when the output is adjusted, that is, when the amplitude of the ultrasonic transducer 5 is adjusted.

Figure 3:
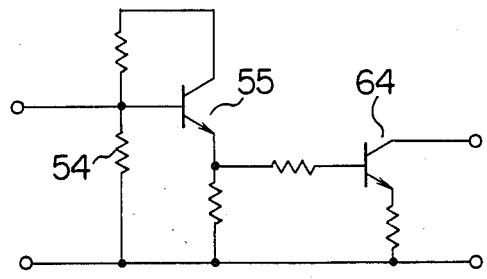
FIG. 3 is a circuit diagram of a known power amplifier circuit.
Figure 4:
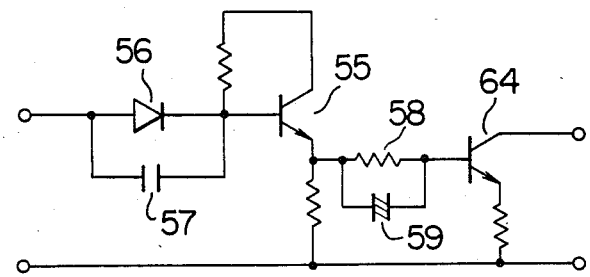
FIG. 4 is a circuit diagram of a power amplifier circuit according to the invention.
Figure 5:
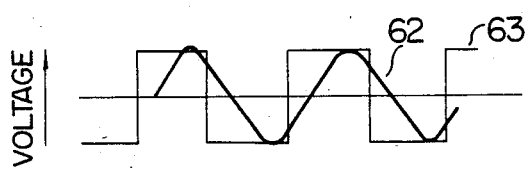
FIG. 5 is a waveform diagram of the known power amplifier circuit.
Figure 6:
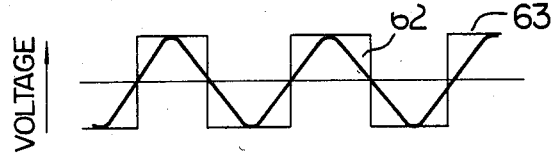
FIG. 6 is a waveform diagram of the power amplifier circuit according to the invention.

As a result, while, with the prior art of FIG. 3, the phase relation between an amplifier circuit output voltage waveform 63 and a feedback voltage waveform 62 becomes as shown in FIG. 5, in accordance with the invention the phase difference between an output voltage waveform 63 and a feedback voltage waveform 62 of the power amplifier circuit 11 is corrected as will be seen from their phase relation shown in FIG. 6.

Figure 7:
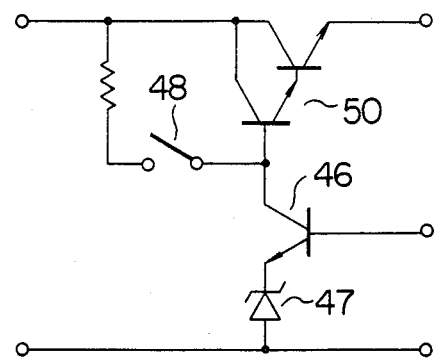
FIG. 7 is a circuit diagram of a known starting circuit.
Figure 8:
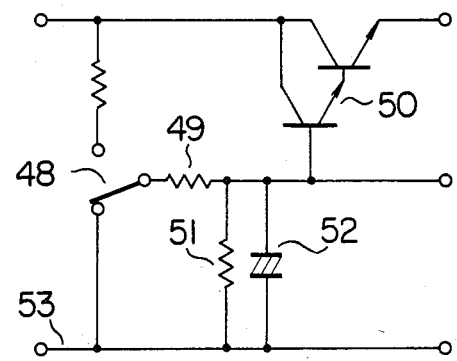
FIG. 8 is a circuit diagram of a starting impulse reducing circuit according to the present invention.
Figure 9:
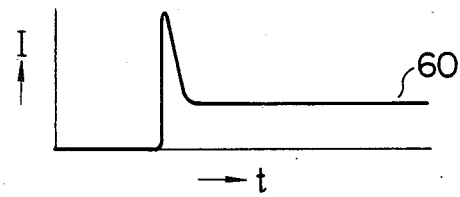
FIG. 9 is a waveform diagram of the known starting circuit.
Figure 10:
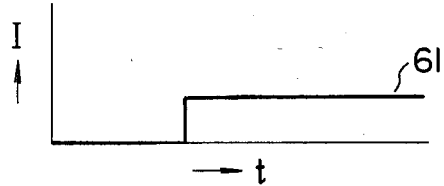
FIG. 10 is a waveform diagram of the starting impulse reducing circuit according to the invention.

Generally, where a high power is generated by the ultrasonic oscillation circuit, during the starting of oscillation the power amplifying element and the ultrasonic transducer 5 are frequently subjected to electric impulses with the resulting deterioration of the performance or damage thereto and also there are many cases where the starting is made difficult when the mechanical vibration system including the ultrasonic transducer 5 and the horn 10 is under load conditions; in accordance with the invention, with a view to overcoming these deficiencies, the starting inpulse reducing circuit 12 is provided so that the power amplifier circuit 11 and the ultrasonic transducer 5 are protected and stabilized and the horn 10 forming the ultrasonic scalpel portion is enabled to start very easily under load conditions. In other words, while it has heretofore been composed of a transistor 46 and a Zener diode 47 of the starting circuit as shown in the prior art of FIG. 7, in the starting inpulse reducing circuit 12 of the invention, as shown in FIG. 8, a resistor 49 is connected in series between a switch 48 and the base of a transistor 50, and a resistor 51 and a capacitor 52 are connected in parallel between the base of the transistor 50 and a connection 53. Thus, when the operator closes the starting switch 48 to start oscillation, the starting circuit prevents any transient circuit from flowing simultaneously with the rise of the voltage. Consequently, while a current waveform 60 from the conventional circuit the prior art of FIG. 7 rises as shown in FIG. 9, the rise of a current waveform 61 from the starting inpulse reducing circuit 12 of the invention becomes flat as shown in FIG. 10.

Moreover, while the power amplifier circuit 11 generates a spike wave which is superposed on the output voltage waveform of the power amplifier circuit 11 or the rectangular wave of an ultrasonic frequency, this spike wave frequently becomes two or more times the rectangular wave tending to cause deterioration of the characteristics of the amplifying element and the ultrasonic transducer 5 or damages thereto and the spike wave suppression circuit 13 is provided to follow the power amplifier circuit 11 thereby suppressing the spike wave and protecting and stabilizing the amplifying element in the power amplifier circuit 11 and the ultrasonic transducer 5. Also, the amplitude adjusting circuit 14 is provided so that the vibration amplitude of the forward end of the horn 10 or the scalpel forward end can be varied continuously and the degree of shattering can be easily adjusted in accordance with the affected part to be operated on.

The ultrasonic scalpel oscillator matching unit 3 includes a matching circuit 15, an amplitude level setting circuit 16, a feedback signal detecting circuit 17, a power detector 18 for detecting the power drawn by the ultrasonic transducer 5, and an amplitude detector 19 for displaying the amplitude of the horn 10. The matching circuit 15 is such that an electric power is supplied with a reduced loss to the ultrasonic transducer 5 without any decrease in the vibration amplitude of the scalpel forward end even if the load on the forward end of the horn 10 or the scalpel forward end is increased and this matching circuit 15 maintains the power of the ultrasonic vibrations against variations in the load of the affected part to be operated on. Moreover, in accordance with the invention it is important to optimize the driving amplitude for ensuring stable operation of the ultrasonic transducer 5 and the amplitude level setting circuit 16 is provided to reduce the loss and stabilize the ultrasonic transducer 5. The feedback signal detecting circuit 17 is one for detecting the resonant frequency and amplitude of the mechanical vibration system which vary in accordance with the load condition on the forward end of the horn 10 and the temperature and its signals are fed back to the preceding amplifying stage or the power amplifier circuit 11 thereby enabling a constant amplitude control and an automatic frequency follow-up.

The ultrasonic scalpel oscillator feedback unit 4 includes a feedback signal Q adjusting circuit 20 and a feedback signal filter circuit 21. Its purpose is such that the resonance frequency and amplitude of the mechanical vibration system detected by the feedback signal detecting circuit 17 are fed back to the power amplifier circuit 11 through the feedback signal Q adjusting circuit 20 and the feedback signal filter circuit 21. While the electrical Q of the feedback circuit must be increased at the start of oscillation so as to ensure a sharp start of ultrasonic oscillation, the electrical Q of the feedback circuit should preferably be lower than the electrical Q at the start of the oscillation to maintain stable vibrations against variations in the load of the horn 10 after the ultrasonic oscillation has come to a steady state and the feed back signal Q adjusting circuit 20 is designed to serve the purpose of automatically adjusting the electrical Q of the feedback circuit and thereby stabilizing the transient state and steady state of the vibrations. On the other hand, the mechanical vibration system including the ultrasonic transducer 5 and the horn 10 frequently includes several spurious frequencies in addition to the main resonant frequency and such spurious frequencies often become a factor which makes the ultrasonic scalpel unstable. In accordance with the invention, the feedback signal filter circuit 21 is used for the purpose of suppressing the spurious frequencies and thereby stabilizing the ultrasonic scalpel.

Then, the handpiece portion of the ultrasonic scalpel according to the invention differs from the conventional one and this will be described first in detail with reference to FIGS. 11 and 12.

Figure 11:
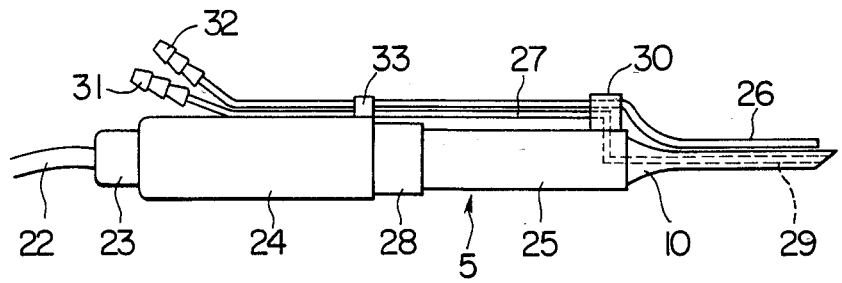
FIG. 11 is an overall view of a handpiece section according to the invention.

FIG. 11 is an overall view of the handpiece portion of the ultrasonic scalpel. The handpiece portion includes mainly a cable 22 connected to the matching unit 3 of the ultrasonic oscillation section, a connector 23, a handle 24, a protective pipe 25, the horn 10 forming the ultrasonic scalpel, an irrigation pipe 26 for supplying a physiological salt solution or the like to an affected part to be operated on, a suction pipe 27 for sucking the liquid substance or the like from the part under going an operation. A connecting pipe 28 is a pipe for mechanically connecting the handle 24 and the protective pipe 25 with screws or the like. The handle 24, the connecting pipe 28 and the protective pipe 25 should preferably be made of a metal which is light and also resisting to corrosion, e.g., aluminum or Duralumin or a synthetic resin which is high in strength, e.g., phenolic resin or ABS resin in order to reduce the weight of the handpiece on the whole and ensure easy and convenient handling by the operator. While the horn 10 forming the ultrasonic scalpel portion is made of a material which satisfactorily transmits high frequency mechanical vibrations and has a resistance to breaking, e.g., Duralumin or titanium alloy, a suction opening 29 is formed inside the horn 10 so as to suck and remove the blood bleeding at the part undergoing an operation, a cleaning physiological salt solution, the cell pieces shattered by the horn 10, etc. A connecting opening 65 in connection with the suction opening 29 is formed to the outer surface of a base 39 of the horn 10, and the connecting opening 65 is connected to the pipe 27 through a pipe joint 30 connected to the outer side of the protective pipe 25 by a suitable method. A suction nipple 31 is connected to the other end of the suction pipe 27 by a suitable method such as soldering or argon welding. Although not shown, the suction nipple 31 is connected to a flexible tube made of a material and having a shape to withstand the suction negative pressure of suction means, e.g., vinyl chloride or silicone resin and connected to the suction means, e.g., a vacuum pump through a trap consisting of a glass bottle or the like which is not shown.

The irrigation pipe 26 is provided for the purpose of supplying an irrigation solution such as physiological salt solution to the part undergoing an operation and it is desirable that the pipe 26 has an open end near the forward end of the horn 10 and it is arranged to be near to the horn 10 without contacting it. Since the horn 10 is set in ultrasonic vibrations, there is the possibility of the irrigation pipe 26 being damaged if it is brought into contact with the horn 10 and there is the possibility of the irrigation pipe 26 becoming a hindrance in the case of microsurgery such as brain surgery if it is excessively apart from the horn 10. The irrigation pipe 26 is fastened or connected to the pipe joint 30 by a suitable method so as to prevent the irrigation pipe 26 from coming into contact with the horn 10 or separating excessively from the horn 10. An irrigation nipple 32 is connected to the other end of the irrigation pipe 26 by a suitable method such as soldering or argon welding. Although not shown, connected to the irrigation nipple 32 is a flexible tube which is medically safe and which is made from vinyl chloride, silicone resin or the like for supplying an irrigation liquid such as physiological salt solution contained in an irrigation liquid container and having a shape to withstand severe handling by a roller type pump such as a peristalsis pump.

A pipe fastener 33 is a fastener for fastening the suction pipe 27 and the irrigation pipe 26 to the handle 24. The material for the suction pipe 27, the irrigation pipe 26, the suction nipple 31, the irrigation nipple 32, the pipe joint 30 and the pipe fastener 33 should preferably be stainless steel or the like having corrosion resistance and elution resistance properties.

Further, the internal construction, vibration characteristic, etc., of the handpiece portion of the ultrasonic scalpel according to the invention will be described in detail with reference to FIG. 12.

Figure 12:
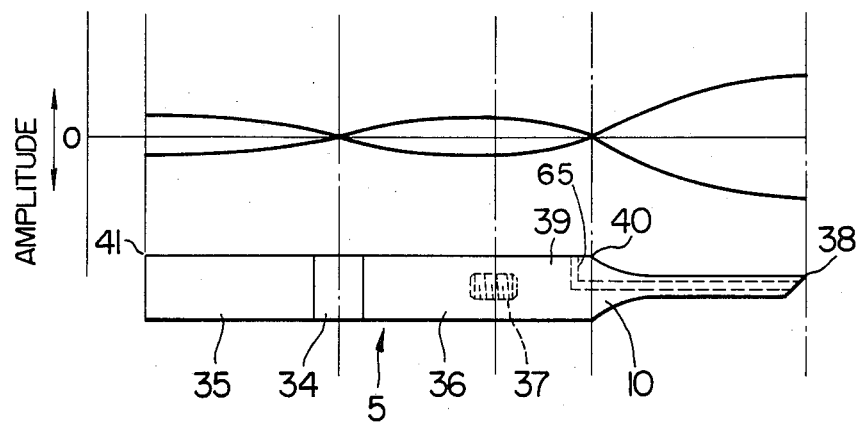
FIG. 12 shows an external view and vibration characteristic of an ultrasonic transducer according to the invention.

The previously mentioned ultrasonic transducer 5 is of the so-called BLT (bolted Langevin type transducer) type transducer construction in which a back plate 35 and a front plate 36, each made of a high tension metal material such as Duralumin or high strength aluminum alloy, are disposed before and back or to the left and right in FIG. 12 of an electrostriction type transducer 34 and the back plate 35, the electrostriction type transducer 34 and the front plate 36 are tightly connected and fastened with each other by bolts made of a high tension metal material and not shown. The front plate 35 and the horn 10 forming the ultrasonic scalpel are firmly coupled together with a plain screw 37 made of a high tension metal material. The electrostriction type transducer 34 should preferably be made of PZT (lead zirconate titanate) and its natural frequency is in the range 1 MHz to 100 MHz, preferably on the order of 10 MHz to 20 MHz. With the back plate 35 and the front plate 36 which are attached to the ends of the electrostriction type transducer 34, their diameters and lengths are determined in such a manner that the frequency of the ultrasonic transducer 5 including the back plate 35, the electrostriction type transducer 34, the front plate 36 and the horn 10 ranges from 20 kHz to 40 kHz, preferably from 23 kHz to 38 kHz. While the shape of the horn 10 is an important factor which determines the amplitude of a forward end 38 of the horn 10, generally the amplitude of the forward end 38 of the horn 10 is inversely proportional to the ratio of the cross-sectional area of a base 39 of the horn 10 to the cross-sectional area of the forward end 38 of the horn 10. The amplitude of the forward end 38 of the horn 10 used for the ultrasonic scalpel of the invention is desirably in the range 50 $\mu$m to 250 $\mu$m, preferably 100 $\mu$m to 150 $\mu$m. Also, the material of the horn 10 is desirably a high tension metal material, preferably titanium alloy.

The ultrasonic transducer 5 employing the electrostriction type transducer 34 made of PZT and forming the ultrasonic scalpel of the invention is advantageous in that it is less susceptible to the load applied to the forward end 38 of the horn 10 compared with other transducers such as a magnetostriction transducer using ferrite and nickel type magnetostriction transducer, that the electric loss is reduced due to the increased mechanical Q, that the heat generation of the transducer is reduced and that satisfactory durability is displayed without using any cooling means, and the ultrasonic transducer 5 is best suited for applications such as an ultrasonic scalpel which must have reliability above all.

Next, the vibration characteristic of the ultrasonic transducer 5 of the invention employing the electrostriction type transducer will be described in reference to FIG. 12. The graph shown in the upper part of FIG. 12 shows the axial amplitude patterns of the various parts of the ultrasonic transducer 5, that is, the amplitude is zero at the axial central portion of the electrostriction type transducer 34, the amplitude is zero at a point 40 of the horn 10 where it starts to constrict and the pattern between the electrostriction transducer 34 and the constriction starting point 40 of the horn 10 takes the form of an arc in which the peak is near a plain screw 37. Also, the pattern between a left end 41 of the back plate 35 and the electrostriction type transducer 34 takes the form of a half arc in which the maximum amplitude is attained at the left end 41 of the back plate 35. Between the constriction starting point 40 of the horn 10 and the forward end 38 of the horn 10 the pattern takes the form of a half arc in which the maximum amplitude is attained at the forward end 38 of the horn 10. Since the magnitude of the amplitude at the forward end 38 of the horn 10, one of the efficiencies of the ultrasonic scalpel, is approximately inversely proportional to the ratio of the cross-sectional area of the base 39 of the horn 10 to the cross-sectional area of the forward end 38 of the horn 10 as mentioned previously, these cross-sectional areas may be varied to provide horn shapes of different amplitudes in accordance with the parts to be treated with the present ultrasonic scalpel, the severity of operations, etc.

Figure 13:
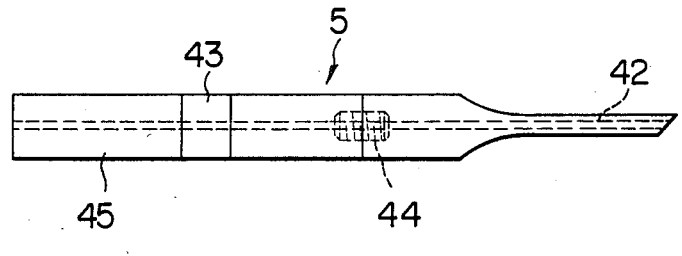
FIG. 13 is an external view of another example of the ultrasonic transducer according to the invention.

Another embodiment of the ultrasonic transducer or the ultrasonic scalpel according to the invention will be described with reference to FIGS. 13 and 11.

Since the vibrator of the ultrasonic transducer or the ultrasonic scalpel according to the invention employs an electrostriction type transducer as mentioned previously, the electric loss of the transducer is reduced with the resulting reduction in the heat generated at the transducer portion and it is also apparent that preferably the durability of the transducer can be improved by far if the heat generated in the vibrator portion is eliminated. Thus, by providing a suction opening 42 extending over the entire axial length of the ultrasonic transducer 5 which has a set of threads in an end of a front plate of the ultrasonic transducer 5 as shown in FIG. 13 so that the irrigation liquid, e.g., physiological salt solution supplied to the affected part operated on is sucked by the suction opening 42 via an irrigation pipe 26 set in the same manner as the irrigation pipe 26 shown in FIG. 11, it is possible to cool a hollow electrostriction type transducer 43. While the hermetic sealing of a plain screw 44 and the suction opening 42 of the hollow electrostriction type transducer 43 is not shown, they may be sealed hermetically by a suitable sealing method such as O-ring or Teflon sealing tapes. Also, while, in FIG. 13, the suction opening 42 is provided to extend over the whole length of the ultrasonic transducer 5 the outlet port of the suction opening may be provided in a direction normal to the axis of the ultrasonic transducer 5 provided it is located on a back plate 45.

As described so far in detail, the ultrasonic oscillation device according to the invention can exhibit a satisfactory function as an ultrasonic scalpel for surgical operation purposes.

We claim:

1. An ultrasonic surgical device having an ultrasonic oscillation circuit and an ultrasonic transducer with an electrostriction type vibrator, said oscillation circuit comprising:

power supply means including a rectifier circuit means for converting AC current from an AC power source into DC current, means for connecting said AC power source and said rectifier circuit means to reduce rush current from said AC power source to said rectifier circuit means;

a smoothing circuit means connected to said rectifier circuit means for reducing ripples of the DC current;

a power amplifier circuit means connected to said smoothing circuit means to produce an amplified electric signal, means connected to said amplifier circuits means for suppressing spike wave of the amplified electric signal, matching-circuit means connected to said spike-suppressing means for supplying an electric signal of a reduced loss to said ultrasonic transducer in response to load increase thereof, means connected to said matching-circuit means for setting an amplitude level of the supplied electric signal to stably operate said transducer with a low loss, means for connecting said amplitude-level setting means and said transducer to drive said transducer and produce a feedback signal, means for feeding back the feedback signal to said power amplifier circuit means, said feedback means including quality-factor adjusting means and feedback signal filtering means for filtering out spurious frequency signals, means connected to said power amplifier circuit means to adjust the amplitude of said amplified electric signal, and starting-impulse reducing means connected between said smoothing circuit means and said power amplifier circuit means to reduce the impulse of the DC current to the latter at start of oscillation.

2. An ultrasonic surgical device as set forth in claim 1, wherein said starting impulse reducing means includes a transistor, a resistor connected in series between an oscillation starting switch and a base of said transistor, and another resistor and a capacitor connected in parallel to the base of said transistor.

3. An ultrasonic surgical device as set forth in claim 1, wherein said power amplifier circuit means includes a parallel circuit of a diode and a capacitor connected in series with a base of an amplifying transistor for the purpose of the stable oscillation of the lower feedback signal, and a parallel circuit of a resistor and another capacitor connected between an emitter of said transistor and a following transistor for the purpose of preventing any deviation of the phase between the amplifier circuit output electric signal and the feedback signal from the feedback means.

4. An ultrasonic surgical device as set forth in claim 1, wherein said ultrasonic transducer includes a horn at a forward end thereof, said horn having a longitudinal axis and wherein the vibrating direction of said horn is substantially parallel to the said longitudinal axis of the said horn wherein a suction opening is formed within said horn and a connecting opening in connection with said suction opening is formed to the outer surface of a base of said horn, and wherein an irrigation pipe is mounted on and arranged at a parallel position near said horn without contacting said horn.

5. An ultrasonic surgical device as set forth in claim 4, wherein said irrigation pipe is adapted to provide a physiological salt solution or the like to an affected part to be operated on, and wherein a forward end of said horn is adapted to contact a tissue of said operated part to thereby shatter said tissue with ultrasonic vibrations and wherein said suction opening is adapted to provide suction and remove said physiological salt solution or the like and cellular pieces and material floated by said ultrasonic vibrations.

6. An ultrasonic surgical device as set forth in claim 6, wherein a material of said horn comprises a titanium alloy.

7. An ultrasonic surgical device as set forth in claim 5, further comprising a housing for said transducer, said housing including a handle and a protective pipe for covering said transducer, and a connecting pipe for coupling said handle and protective pipe, said pipes and handle being made of a metal which is light and resistant to corrosion.

8. An ultrasonic surgical device as set forth in claim 1, wherein a suction opening is formed through the whole axial length of said ultrasonic transducer, a set of threads is formed in an end of a front plate of said ultrasonic transducer, a suction opening is formed through the whole axial length of a horn, and said horn is connected to said ultrasonic transducer with a screw whereby a continuous suction path is formed.

9. An ultrasonic surgical device as set forth in claim 8, wherein said irrigation pipe is adapted to provide a physiological salt solution or the like to an affected part to be operated on, and wherein a forward end of said horn is adapted to contact a tissue of said operated part to thereby shatter said tissue with ultrasonic vibrations and wherein said suction opening is adapted to provide suction and remove said physiologic salt solution or the like and cellular pieces and material floated by said ultrasonic vibrations.

* * * * *